US009421346B2

(12) United States Patent
Callahan et al.

(10) Patent No.: US 9,421,346 B2
(45) Date of Patent: Aug. 23, 2016

(54) IUPC INTRODUCER

(75) Inventors: Mark J. Callahan, Medway, MA (US);
Linda D'Elia, Westfield, MA (US);
Mary Jo Griffin, Bellingham, MA (US)

(73) Assignee: Covidien LP, Mansfield, MA (US)

( * ) Notice: Subject to any disclaimer, the term of this patent is extended or adjusted under 35 U.S.C. 154(b) by 1320 days.

(21) Appl. No.: 12/424,707

(22) Filed: Apr. 16, 2009

(65) Prior Publication Data

US 2010/0268123 A1    Oct. 21, 2010

(51) Int. Cl.
*A61M 25/06*    (2006.01)

(52) U.S. Cl.
CPC ....... *A61M 25/0668* (2013.01); *A61M 25/0662* (2013.01); *A61M 2025/0675* (2013.01); *A61M 2025/0681* (2013.01); *A61M 2025/0687* (2013.01)

(58) Field of Classification Search
CPC ................ A61M 25/0662; A61M 25/0668; A61M 25/0681; A61M 25/0687; A61M 2025/0675
USPC .................. 600/585, 588; 128/839, 840, 841
See application file for complete search history.

(56) References Cited

U.S. PATENT DOCUMENTS

| 3,989,038 | A |   | 11/1976 | Neward |   |
|---|---|---|---|---|---|
| 4,136,681 | A |   | 1/1979 | Hon |   |
| 4,252,131 | A |   | 2/1981 | Hon et al. |   |
| 4,325,387 | A |   | 4/1982 | Helfer |   |
| 4,356,610 | A |   | 11/1982 | Hon et al. |   |
| 4,644,957 | A | * | 2/1987 | Ricciardelli et al. | 600/376 |
| 4,722,730 | A |   | 2/1988 | Levy et al. |   |
| 4,738,666 | A |   | 4/1988 | Fuqua |   |
| 4,747,833 | A | * | 5/1988 | Kousai et al. | 604/164.05 |

(Continued)

FOREIGN PATENT DOCUMENTS

| EP | 0 064 212 A2 | 11/1982 |
|---|---|---|
| EP | 0 279 015 A2 | 8/1988 |

(Continued)

OTHER PUBLICATIONS

European Search Report dated Sep. 28, 2010 for copending European Appln. No. 10 156 063.

(Continued)

*Primary Examiner* — Adam J Eiseman

(57) ABSTRACT

An introducer adapted to facilitate positioning of a catheter, such as an intrauterine catheter, is provided. The introducer includes an elongate member having an outer wall defining a longitudinal axis and a longitudinal lumen for reception of a catheter, e.g., an intrauterine catheter. The outer wall includes first and second longitudinal edges defining a longitudinal slot in communication with the longitudinal lumen. The outer wall has a cross-section orthogonal to the longitudinal axis and defining a thickness at an opposed location generally opposing the longitudinal slot greater than a thickness at edge locations adjacent the first and second longitudinal edges, to thereby permit the first and second longitudinal edges to be displaced relative to each other to increase a dimension of the longitudinal slot to facilitate one of removal or insertion of the catheter via the longitudinal slot and relative to the longitudinal lumen. The thickness of the outer wall may be dimensioned to gradually decrease from the opposed location to the edge locations. The ratio of the thickness of the outer wall at the opposed location to the thickness of the outer wall at the edge locations is about 2:1. The outer wall may define a generally c-shaped cross-section.

7 Claims, 2 Drawing Sheets

(56) References Cited

U.S. PATENT DOCUMENTS

| | | | |
|---|---|---|---|
| 4,781,690 A * | 11/1988 | Ishida et al. | 604/164.05 |
| 4,874,374 A * | 10/1989 | Kousai et al. | 604/164.05 |
| 5,104,388 A | 4/1992 | Quackenbush | |
| 5,566,680 A | 10/1996 | Urion et al. | |
| 5,984,879 A | 11/1999 | Wallace et al. | |
| 6,115,624 A | 9/2000 | Lewis et al. | |
| 6,231,524 B1 | 5/2001 | Wallace et al. | |
| 7,137,995 B2 * | 11/2006 | Studin | 623/8 |
| 2002/0165489 A1 * | 11/2002 | McGuckin et al. | 604/109 |
| 2003/0032941 A1 | 2/2003 | Boyle | |

FOREIGN PATENT DOCUMENTS

| | | |
|---|---|---|
| EP | 0450 221 A1 | 10/1991 |
| JP | 54-137889 | 10/1979 |
| JP | 11-505136 | 5/1999 |
| JP | 2004-500166 | 1/2004 |
| WO | WO 96/33664 | 10/1996 |
| WO | WO 01/34238 | 5/2001 |

OTHER PUBLICATIONS

Response filed on Apr. 7, 2014 for European Patent Application No. 10156063.9-1257, 12 pages.
Office Action dated May 27, 2015 for Japanese Patent Application No. 2014-54429; 3 pages.
Office Action dated May 27, 2015 for Japanese Patent Application No. 2010-86589; 6 pages.
Examination Report dated Feb. 4, 2014 for EP Application No. 10156063.90, filed Mar. 10, 2010, 4 pages.
Response and Argument, including translation of claims, filed Mar. 18, 2014 to Office Action dated Jan. 6, 2014 for JP Patent Application No. 2010-086589, filed Apr. 2, 2010, 6 pages.
Notice of Acceptance dated Feb. 20, 2014 for Australian Patent Application No. 2010201011, filed Mar. 16, 2010, 2 pages.
Office Action with translation dated Aug. 29, 2014 for Japanese Patent Application No. 2010-086589, 5 pages.
Response to Office Action With English translation filed on Nov. 12, 2014 for Japanese Patent Application No. 2010-86589; 6 pages.
Response to Office Action with English Claims flied Jul. 24, 2015 for Japanese Appiication No. 2010-86589; 8 pages.
Office Action with translation dated Jan. 6, 2014 for JP Patent Application No. 2010-086589, filed Apr. 2, 2010, 5 pages.
Response to Examiner's Report dated Nov. 5, 2013 for Australian Application No. 2010201011, filed Apr. 16, 2009, 10 pages.
Examination Report dated May 31, 2013 for Australian Patent Application No. 2010201011, filed Mar. 26, 2010, 4 pages.
Office Action from counterpart Canadian Application No. 2,696,218 dated Feb. 10, 2016, 3 pages.

* cited by examiner

IUPC INTRODUCER

TECHNICAL FIELD

The present disclosure relates to an intrauterine pressure catheter (IUPC) system. The present disclosure also relates to an introducer for positioning a catheter within the uterus and for permitting the efficient removal of the introducer after application of the catheter.

DESCRIPTION OF THE RELATED ART

Systems for monitoring and/or analyzing fetal contractions include externally applied devices (e.g., tocodynamometers) and intrauterine devices. External devices, such as a tocodynamometer or tocotransducer, sense uterine activity superficially and non-invasively. Tocodynamometers are held adjacent the patient's abdomen in the vicinity of the fundus and measure the hardness of the abdominal wall which is an indication of uterine activity. Such devices, however, may suffer from large measurement errors.

Intrauterine pressure monitoring systems provide more reliable and accurate information regarding uterine contractions including frequency, duration, intensity, and resting tone of the uterine contractions. Intrauterine devices also reduce measurement errors relative to external devices because the uterine pressure is measured directly with a catheter appropriately positioned within the uterus.

SUMMARY

Accordingly, an introducer adapted to facilitate positioning of a catheter is provided. The introducer includes an elongate member having an outer wall defining a longitudinal axis and a longitudinal lumen for reception of a catheter, e.g., an intrauterine catheter. The outer wall includes first and second longitudinal edges defining a longitudinal slot in communication with the longitudinal lumen. The outer wall has a cross-section orthogonal to the longitudinal axis and defining a thickness at an opposed location generally opposing the longitudinal slot greater than a thickness at edge locations adjacent the first and second longitudinal edges, to thereby permit the first and second longitudinal edges to be displaced relative to each other to increase a dimension of the longitudinal slot to facilitate one of removal or insertion of the catheter via the longitudinal slot and relative to the longitudinal lumen. The thickness of the outer wall may be dimensioned to gradually decrease from the opposed location to the edge locations. The ratio of the thickness of the outer wall at the opposed location to the thickness of the outer wall at the edge locations is about 2:1. The outer wall may define a generally c-shaped cross-section.

The elongate member may define an atraumatic leading tip segment. The leading tip segment includes first and second oblique edges leading to an arcuate leading surface to define a generally open profile. The open profile may accommodate a pressure sensor associated with the catheter. The elongate member may include a grip to facilitate manipulating of the outer wall and separation of the introducer from the catheter.

In an alternative embodiment, an intrauterine pressure catheter monitoring system is provided. The system includes a catheter having a pressure sensor for detecting biomedical signals indicative of uterine activity, an introducer having an outer wall defining a longitudinal axis and a longitudinal lumen for reception of the catheter, and an external monitor adapted to receive the biomedical signals and having logic and associated output for display of information retrieved by the biomedical signals. The outer wall of the introducer may include first and second longitudinal edges defining a longitudinal slot in communication with the longitudinal lumen. The outer wall has a cross-section orthogonal to the longitudinal axis defining a thickness at an opposed location generally opposing the longitudinal slot greater than a thickness at edge locations adjacent the first and second longitudinal edges, to thereby permit the first and second longitudinal edges to be displaced relative to each other to increase a dimension of the longitudinal slot to facilitate one of removal or insertion of the catheter via the longitudinal slot and relative to the longitudinal lumen.

BRIEF DESCRIPTION OF THE DRAWINGS

Embodiments of the present disclosure will be better appreciated by reference to the drawings wherein.

DETAILED DESCRIPTION OF THE EMBODIMENTS

Figure 1:
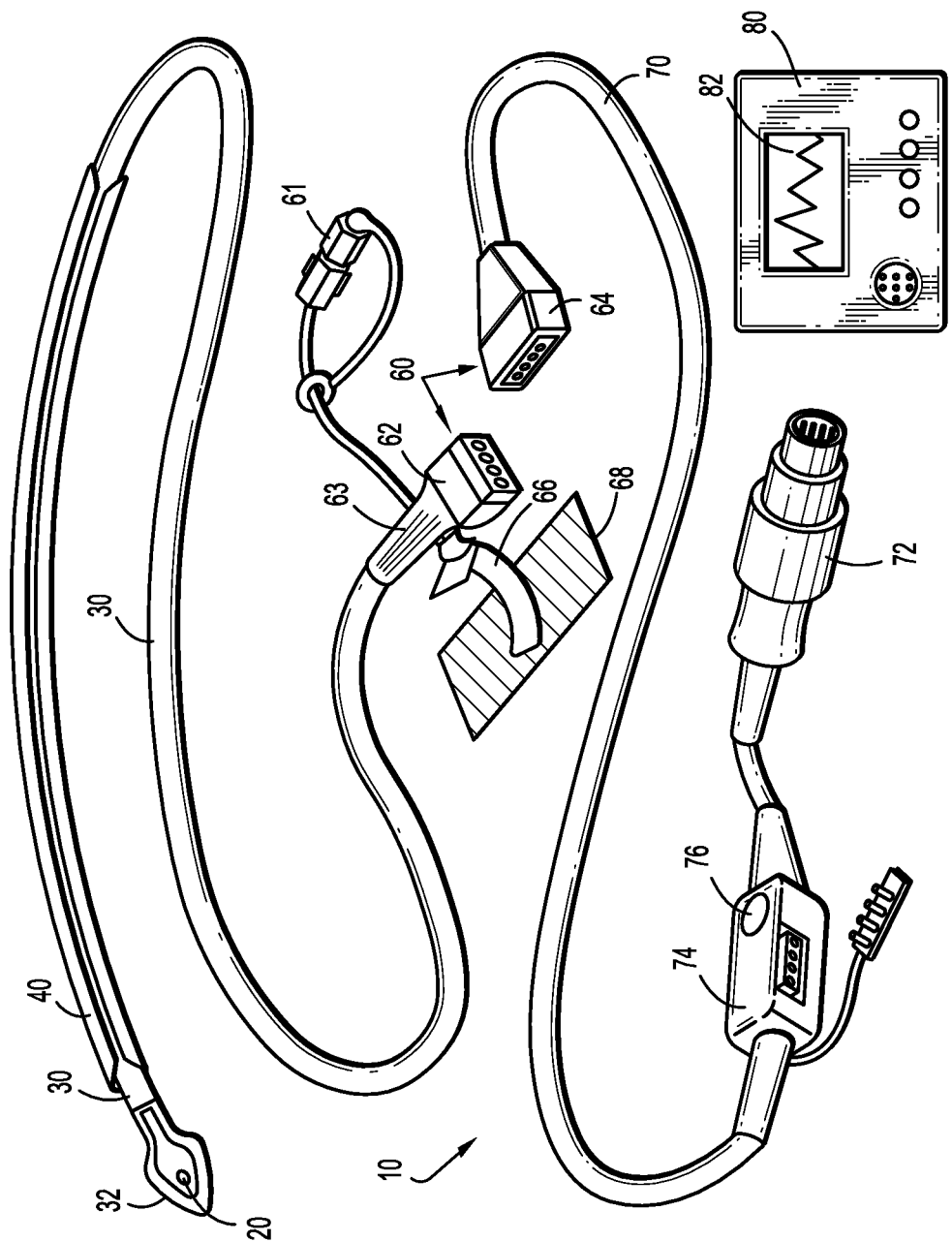
FIG. 1 is a perspective view of an intrauterine pressure catheter system in accordance with the present disclosure.

Referring now to the drawings, in which like reference numerals identify identical or substantially similar parts throughout the several views, FIG. 1 illustrates, in perspective view, an intrauterine pressure catheter system 10 in accordance with the principles of the present disclosure. Intrauterine pressure catheter system 10 may include pressure sensor 20, catheter 30, introducer 40, connector assembly 60, monitor cable 70, and external monitor 80. Pressure sensor 20 may be embedded in tip 32 of catheter 30. In the alternative, pressure sensor 20 may be a separate component and positionable within a lumen of catheter 30. Introducer 40 facilitates insertion of catheter 30 and proper positioning of tip 32 and therefore, pressure sensor 20, at a defined therapeutic position within the uterus. Introducer 40 will be discussed in greater detail hereinbelow.

Catheter 30 may be any suitable intrauterine catheter such as, e.g., the catheter disclosed in commonly assigned U.S. Pat. No. 5,566,680 to Urion et al., the entire contents of which are hereby incorporated by reference herein. Catheter 30 may be relatively flexible to permit the catheter 30 to follow the contours of the cervix.

Connector assembly 60 includes female connector socket 62 and male connector plug 64 which electrically connects pressure sensor 20 with monitor cable 70. Monitor cable 70 electrically connects pressure sensor 20 to external monitor 80 via monitor pin connector 72. Test member 74 may be provided to assure that male connector plug 64, monitor cable 70, and monitor pin connector 72 are operational and properly connected. Push button 76 can be depressed to clear data or zero system 10 at any time during use. Connector assembly 60 is secured to the thigh or abdomen of the patient using adhesive attachment pad 66 and an attachment strap 68 subsequent to placement of catheter 30. To permit infusion of fluid into the amniotic sac, a luer fitting 61 is connected to catheter 30 in the body 63 enclosing female connector socket 62.

Figure 2:
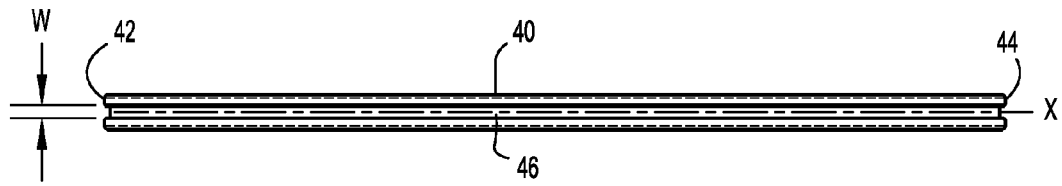
FIG. 2 is a top view of the introducer of the system of FIG. 1.
Figure 3:
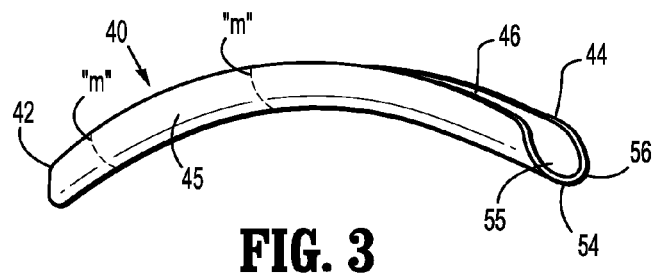
FIG. 3 is a perspective view of an alternate embodiment of the introducer.
Figure 4:
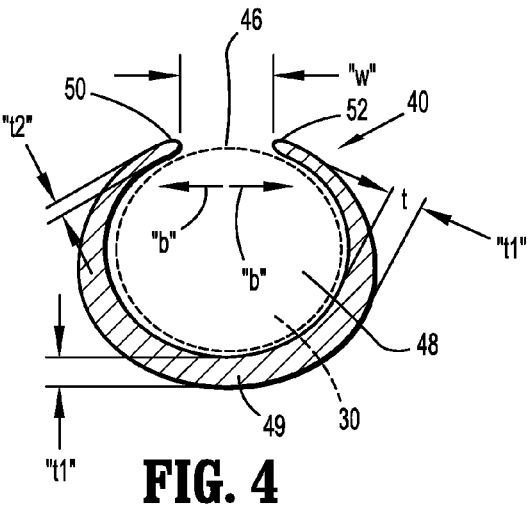
FIG. 4 is a cross-sectional view of the introducer of the system of FIG. 1.

With reference to FIG. 2 and FIG. 4, in conjunction with FIG. 1, introducer 40 will be discussed. Introducer 40 is adapted for receiving catheter 30 to facilitate insertion of the catheter 30 within the uterus. Introducer 40 is of sufficient stiffness and/or rigidity to facilitate advancement within the uterus and to ease insertion of catheter 30. Introducer 40 includes outer wall 45 defining a longitudinal axis "x" along the length of introducer 40 from proximal or trailing end 42 to distal or leading end 44. Introducer 40 has longitudinal slot 46 within outer wall 45 disposed along at least a portion of the length of introducer 40. Outer wall 45 defines longitudinal lumen 48 which receives catheter 30. Catheter 30 may be installed into, and removed from, longitudinal lumen 48 via longitudinal slot 46. Longitudinal slot 46 defines a width "w", which, in combination with other features of outer wall 45 to be discussed hereinbelow, permits insertion or removal of catheter 30 from introducer 40. Width "w" of longitudinal slot 46 may be about 0.105 inches to about 0.165 inches, or from about 0.125 inches to about 0.145 inches. As will be appreciated, width "w" may be increased by deflection of longitudinal edges 50, 52 defining slot 46. Introducer 40 may be shaped as shown or may have a gentle curve, as illustrated in FIG. 3, to conform to the shape of the vagina and cervix. Longitudinal lumen 48 defines an internal dimension or diameter to receive catheter 30. In one embodiment, the internal diameter of longitudinal lumen 48 generally approximates the outer diameter of catheter 30 as shown in phantom in FIG. 4.

Referring now to FIG. 4, introducer 40 has a cross-section transverse to longitudinal axis "x". The cross-section may define a generally arcuate configuration, such as a c-shape, a u-shape, or a horseshoe-shape. Other shapes are also envisioned to those skilled in the art, such as circular, ovoid, and the like. As mentioned hereinabove, introducer 40 includes longitudinal edges 50, 52 within outer wall 45, which define longitudinal slot 46. The thickness "t1" of introducer 40 is broadest at location 49 opposite slot 46 and along the arc section towards longitudinal edges 50 and 52. In embodiments, thickness "t1" is about 0.030 inches. The thickness tapers towards longitudinal edges 50, 52 to a thickness "t2". In embodiments, thickness "t2" is about 0.015 inches. In embodiments, the ratio between "t1" and "t2" is about 4:1, or alternatively, about 3:1, about 2:1 or about 1.5:1. The thickness may taper in linear or gradual manner from location 49 toward longitudinal edges 50, 52, or may be non-linear. The arrangement permits longitudinal edges 50, 52 to be displaced relative to each other in opposed direction "b" to facilitate reception or removal of catheter 30 relative to longitudinal lumen 48 via longitudinal slot 46. For example, due to the more narrow thickness of the segment of outer wall 45 adjacent longitudinal edges 50, 52, the edges 50, 52 may deflect outwardly or inwardly in at least the direction of arrow "b" to permit the passage of catheter 30.

Figure 5:
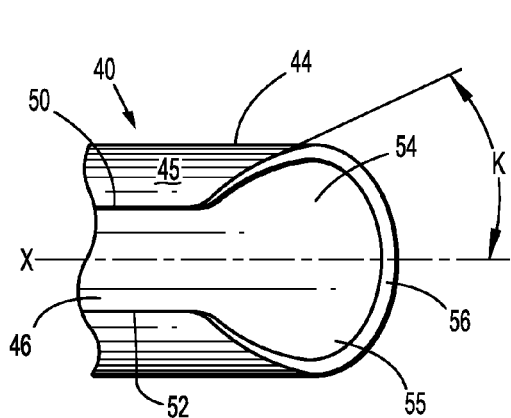
FIG. 5 is a top view of the distal or leading end of the introducer illustrating the atraumatic tip.

Introducer 40 may include an atraumatic tip 54 as shown in FIGS. 3 and 5 adjacent distal or leading end 44. Atraumatic tip 54 is adapted to reduce discomfort or tissue damage when advancing introducer 40 through tissue. Atraumatic tip 54 defines an opening 55 having curved leading edge 56 and oblique edges 57 extending contiguously from the leading edge 56. The curve of leading edge 56 minimizes the risk of tissue trauma. Leading edge 56 may also be formed from a soft, flexible material capable of deforming as it contacts tissue. Oblique edges 57 may be arranged at an angle "k" ranging from about 10° to about 60° relative to the longitudinal axis "x". Atraumatic tip 54 may be integrally formed with introducer 40 or may be formed separate therefrom. When formed as a separate component, atraumatic tip 54 may be coupled to introducer 40 by any suitable means, such as, for example, with the use of adhesives or heat welding. Opening 55 of atraumatic tip 54 may accommodate pressure sensor 20. Oblique edges 57 may assist in removal of introducer 40 from catheter 30 and pressure sensor 20.

Figure 6:
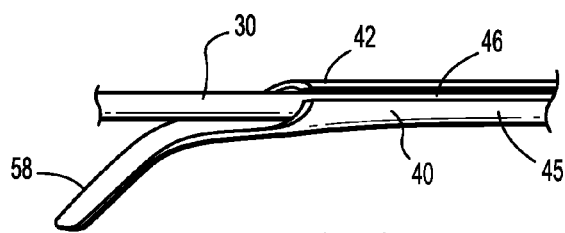
FIG. 6 is a perspective view illustrating the grip of the introducer.

Introducer 40 includes a grip as shown in FIG. 6 to ease removal of introducer 40 from catheter 30. Grip 58 may be a tab, flap, strip, or other arm adjacent proximal end 42. In embodiments, grip 58 may be a bend in proximal end 42. Grip 58 is angled from longitudinal axis "x". In embodiments, grip 58 is at about a 45 degree angle from longitudinal axis "x". Grip 58 permits the clinician to grasp and pull introducer 40 away from catheter 30 in a direction opposite longitudinal slot 46 of introducer 40. In embodiments, grip 58 may have finger catching surfaces or be textured to facilitate engagement by the clinician. Grip 58 may be integrally formed with introducer 40 or may be formed separate therefrom. When formed as a separate component, grip 58 may be coupled to introducer 40 by any suitable means, such as, for example, use of adhesives or heat welding. Introducer 40 may further include depth markings "m" on the external surface of outer wall 45 (FIG. 3). Depth markings "m" may correspond to various predefined distances measured from atraumatic tip 54 to assist the surgeon in ascertaining the degree of insertion of introducer 40 within the cervix.

Introducer 40 may be fabricated from material sufficiently rigid to endure placement and manipulation without loss of structural integrity. Introducer 40 may be fabricated of lubricious materials to reduce the coefficient of friction upon exposure to tissue. Introducer 40 may be a plastic resin, polyethylene, polyvinylchloride, silicone, Teflon™, or combinations thereof. In embodiments, introducer 40 may be made from a medical grade metal or polymer and have a lubricious coating made from one or more of the materials described above.

An anti-bacterial coating may be applied on the entire disposable portion of intrauterine pressure catheter system 10. Such a coating provides an antiseptic surface active against major nosocomial pathogens. For example, a chlorhexidine and silver sulfadiazine coating can be molecularly bonded to the surface of catheter 30 and introducer 40.

Referring again to FIG. 1, monitor 80 includes circuitry or logic adapted to receive biomedical signals collected by pressure sensor 20 and provide an output either text or visual on display 82.

The use of intrauterine pressure catheter system 10 of the present disclosure will be discussed. The components of the system are connected and prepared for use. Monitor pin connector 72 is plugged into external monitor 80. If desired, test member 74 may be used to assure that monitor cable 70, male connector plug 64, and monitor pin connector 72 are operational. Previously obtained data within monitor 80 is then cleared or zeroed by pressing push button 76 on test member 74. Monitor cable 70 is connected, via male connector plug 64, to female connector socket 62 and connector assembly 60 is completed. External monitor 80 is activated.

In one methodology, catheter 30 is assembled within introducer 40 with catheter tip 32 being positioned adjacent the distal end 44 of introducer 40. In this regard, pressure sensor 20 may be disposed adjacent opening 55 of introducer 40. Catheter 30 may be assembled within introducer 40 by sliding catheter along longitudinal lumen 48, or, alternatively, by introducing catheter 30 through longitudinal slot 46. First and second edges 50, 52 may deflect to accommodate catheter 30 as discussed hereinabove. Introducer 40 and catheter 30 are then inserted by gently sliding the components through the cervical os and into the amniotic space. Depth markings "m" on outer wall of introducer 40 may assist the clinician in appropriately positioning atraumatic tip 54 at the proper location. Alternatively, first and second position indicators on catheter 30 indicate insertion depths of 12 and 18 inches, respectively, relative to the introitus. Catheter 30 is advanced until the second position indicator, the 18 inch mark, is at the introitus. The second position indicator indicates that catheter tip 32 has progressed about 12-14 inches into the uterus and should be positioned at the fundus of the uterus. In another method, introducer 40 may be first introduced within the cervix. Once appropriately positioned as confirmed by, e.g., depth markings "m", catheter 30 may be advanced though longitudinal lumen 48 of introducer 40 whereby pressure sensor 20 is disposed adjacent atraumatic tip 54.

Once catheter 20 is properly positioned, introducer 40 may be removed. Holding introducer 40 in one hand and catheter 30 in the other, introducer 40 is retracted and separated from catheter 30. In embodiments, introducer 40 may be separated from catheter 30 via grip 58. Introducer 40 may be separated from catheter 30 by sliding introducer 40 longitudinally along a portion of catheter 30 thereby separating introducer 40 from catheter 30 via the opening in distal end 44 and slot 46, by pulling or otherwise separating the introducer from catheter 30 via longitudinal slot 46 where longitudinal edges 50, 52 deflect to permit passage of catheter 30, and/or by combinations of these methods. In addition, the angled arrangement of longitudinal edges 50, 52 may enable atraumatic tip 54 to slide along pressure sensor 20 to permit passage of the pressure sensor 20. With catheter 30 now positioned within the cervix, adhesive attachment pad 66 is applied to the patient's thigh or abdomen and attachment strap 68 is secured to adhesive attachment pad 66. Attachment strap 68 is adjusted as desired for patient comfort. Monitoring of uterine activity with pressure sensor 20 and monitor 80 is commenced.

It will be understood that various modifications may be made to the embodiments disclosed herein. Therefore, the above description should not be construed as limiting, but merely as an exemplification of preferred embodiments. Those skilled in the art will envision other modifications within the scope and spirit of the present disclosure. Such modifications and variations are intended to come within the scope of the following claims.

What is claimed is:

1. An introducer adapted to facilitate positioning of a catheter into a cavity of a patient, which comprises:
an elongate member including an outer wall defining a longitudinal axis and having a longitudinal lumen for reception of a catheter, the outer wall including first and second longitudinal edges defining a longitudinal slot in communication with the longitudinal lumen, the outer wall having a cross-section orthogonal to the longitudinal axis and defining a thickness at an opposed location generally opposing the longitudinal slot greater than a thickness at edge locations adjacent the first and second longitudinal edges, the outer wall being dimensioned to gradually and continuously decrease in thickness from the opposed location to the edge locations, to thereby permit the first and second longitudinal edges to be displaced relative to each other to increase a dimension of the longitudinal slot to facilitate one of removal or insertion of the catheter via the longitudinal slot and relative to the longitudinal lumen, and wherein the elongate member defines a leading tip segment that includes first and second oblique edges that are arranged at an angle ranging from 10° to 60° relative to the longitudinal axis.

2. The introducer according to claim 1 wherein the ratio of the thickness of the outer wall at the opposed location to the thickness of the outer wall at the edge locations is about 2:1.

3. The introducer according to claim 1 wherein the outer wall defines a generally c-shaped cross-section.

4. The introducer according to claim 1 wherein the leading tip segment is atraumatic and includes a curved leading edge, and the first and second oblique edges extending therefrom.

5. The introducer according to claim 1 wherein the elongate member includes a grip.

6. The introducer according to claim 1, wherein the catheter is an intrauterine catheter.

7. An intrauterine pressure catheter monitoring system, which comprises:
a catheter including a pressure sensor for detecting biomedical signals indicative of uterine activity;
an introducer comprising an elongate member including an outer wall defining a longitudinal axis and having a longitudinal lumen for reception of the catheter, the outer wall including first and second longitudinal edges defining a longitudinal slot in communication with the longitudinal lumen, the outer wall having a cross-section orthogonal to the longitudinal axis and defining a thickness at an opposed location generally opposing the longitudinal slot greater than a thickness at edge locations adjacent the first and second longitudinal edges, the outer wall being dimensioned to gradually and continuously decrease in thickness from the opposed location to the edge locations to thereby permit the first and second longitudinal edges to be displaced relative to each other to increase a dimension of the longitudinal slot to facilitate one of removal or insertion of the catheter via the longitudinal slot and relative to the longitudinal lumen and wherein the elongate member defines a leading tip segment that includes first and second oblique edges that are arranged at an angle ranging from 10° to 60° relative to the longitudinal axis; and
an external monitor adapted to receive the biomedical signals and having logic and associated output for display of information retrieved by the biomedical signals.

* * * * *